(12) United States Patent
Magnuson

(10) Patent No.: US 8,470,021 B2
(45) Date of Patent: Jun. 25, 2013

(54) RADIALLY EXPANDABLE STENT

(75) Inventor: Mark A. Magnuson, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 453 days.

(21) Appl. No.: 12/341,253

(22) Filed: Dec. 22, 2008

(65) Prior Publication Data

US 2009/0171426 A1 Jul. 2, 2009

Related U.S. Application Data

(60) Provisional application No. 61/017,440, filed on Dec. 28, 2007.

(51) Int. Cl.
*A61F 2/82* (2006.01)

(52) U.S. Cl.
USPC .......................... 623/1.16; 623/1.17

(58) Field of Classification Search
USPC .................. 623/1.15–1.18, 1.3–1.32
See application file for complete search history.

(56) References Cited

U.S. PATENT DOCUMENTS

| | | | |
|---|---|---|---|
| 5,102,417 A * | 4/1992 | Palmaz | ......................... 606/195 |
| 5,449,373 A | 9/1995 | Pinchasik et al. | |
| 5,827,321 A | 10/1998 | Roubin et al. | |
| 5,836,964 A | 11/1998 | Richter et al. | |
| 5,853,419 A | 12/1998 | Imran | |
| 5,860,999 A | 1/1999 | Schnepp-Pesch et al. | |
| 5,861,027 A | 1/1999 | Trapp | |
| 6,174,326 B1 | 1/2001 | Kitaoka et al. | |
| 6,179,868 B1 | 1/2001 | Burpee et al. | |
| 6,200,334 B1 | 3/2001 | Jang | |
| 6,264,688 B1 | 7/2001 | Herklotz et al. | |
| 6,299,635 B1 | 10/2001 | Frantzen | |
| 6,682,554 B2 | 1/2004 | Oepen et al. | |
| 6,764,506 B2 | 7/2004 | Roubin et al. | |
| 6,786,922 B2 | 9/2004 | Schaeffer | |
| 6,875,228 B2 | 4/2005 | Pinchasik et al. | |
| 7,056,337 B2 | 6/2006 | Boatman | |
| 2001/0047200 A1 | 11/2001 | White et al. | |
| 2003/0105517 A1 | 6/2003 | White et al. | |
| 2007/0213810 A1 * | 9/2007 | Newhauser et al. | ......... 623/1.16 |

* cited by examiner

*Primary Examiner* — Elizabeth Houston
(74) *Attorney, Agent, or Firm* — Brinks Hofer Gilson & Lione

(57) ABSTRACT

An expandable stent radially adjustable between a collapsed state and an expanded state. The stent generally includes a main body and a plurality of connector segments. The main body has first and second ends, a longitudinal axis extending from the first end to the second end, and a plurality of ring structures. Each of the plurality of connector segments joins adjacent ring structures. Some ring structures may be connected by a pair of diamond connector segments that define a diamond-shaped portion when the stent is in the expanded state. Some ring structures may be connected by flex connector segments oriented to permit rotation of the second ring structure about the longitudinal axis during radial expansion of the stent.

14 Claims, 10 Drawing Sheets

RADIALLY EXPANDABLE STENT

CROSS-REFERENCE TO RELATED APPLICATION

This patent application claims the benefit under 35 U.S.C. §119(e) of U.S. provisional patent application Ser. No. 61/017,440, filed Dec. 28, 2007 and entitled RADIALLY EXPANDABLE STENT, the entire contents of which are incorporated herein by reference.

BACKGROUND

The present invention relates generally to the field of intraluminal support devices, or stents. More particularly, the present invention relates to self-expanding and balloon expandable stents having a ring structure architecture.

Various types of disease conditions present clinical situations in which a vessel of a patient needs to be artificially supported to maintain an open passageway through which fluids, such as blood, can flow. For example, blood flow through an artery can be impeded due to a build-up of cholesterol on the interior wall of the vessel. Also, vessel walls can be weakened be a variety of conditions, such as aneurysms.

Intraluminal support frames, sometimes referred to as stents, provide an artificial mechanism to support a body vessel. Stents are typically tubular-shaped members that are placed in the lumen of the vessel and, once deployed, exert a radially-outward directed force onto the vessel wall to provide the desired support.

Stents are typically positioned at the point of treatment by navigation through the vessel, and possibly other connected vessels, until the point of treatment is reached. This navigation requires the stent to be able to move axially through the vessel(s) prior to deployment, while still maintaining the ability to exert an outward force on the interior wall once deployed. Accordingly, stents typically have radially collapsed and expanded states. In the collapsed state, the stent has a relatively small diameter that allows it to move axially through the vessel. In the expanded state, the stent has a relatively large diameter that allows it to exert an outward force on the interior wall of the lumen, thereby providing the desired support to the vessel. During navigation through the vessel(s), the collapsed stent will likely encounter various turns and bends. Therefore, it is desirable for the collapsed stent to exhibit at least a minimum degree of axial flexibility along the longitudinal length of the stent.

Many stents longitudinally contract while radially expanding, thereby affecting the size of the body vessel that is treated or affected by the stent. As a result of this longitudinal contraction, medical professionals may insert into a patient a stent having a collapsed length that is longer than the length of the portion of the body vessel that is to be treated, thereby potentially increasing the difficulty of advancing the stent through the various turns and bends leading to the treated area. Therefore, it is desirable to minimize longitudinal contraction of the stent during radial expansion.

Stents are often formed by removing material from a cannula, such as a piece of tubing, so that the cannula becomes expandable. The size and strength of a particular stent is typically related to the size of the piece of tubing from which the stent is formed. For example, a stent formed from a larger piece of tubing will generally exhibit a greater radial strength than a stent formed from a smaller piece of tubing. However, a stent formed from smaller piece of tubing will generally have a smaller collapsed state diameter than a stent formed from a larger piece of tubing.

It is therefore desirable to provide a stent having a sufficient radial strength in its expanded state and a sufficiently small diameter in its collapsed state, while exhibiting a minimum degree axial flexibility along the longitudinal length thereof and while maintaining a generally constant length while radially expanded from the collapsed state to the expanded state.

SUMMARY

In overcoming the limitations and drawbacks of the prior art, the present invention provides an expandable stent that is radially adjustable between a collapsed state and an expanded state. The stent generally includes a main body and a plurality of connector segments. The main body has first and second ends and a longitudinal axis extending from the first end to the second end. The main body also includes a plurality of ring structures, each of which defines an undulating pattern. Each of the plurality of connector segments joins adjacent ring structures. A pair of diamond connector segments joins first and second ring structures and cooperates with at least one of the first and second ring structures to define a diamond-shaped portion when the stent is in the expanded state.

The undulating pattern of each of the plurality of ring structures includes a plurality of middle portions connected with each other by a plurality of end portions. The pair of diamond connector segments may both be connected to an end portion of the first ring structure and may be respectively connected to adjacent end portions of the second ring structure.

In one design, the diamond connector segments cooperating with the first and second ring structures define two diamond-shaped portions when the stent is in the expanded state.

In another aspect, the expandable stent includes a main body with at least first, second, and third ring structures; and a plurality of connector segments with at least first and second sets of flex connector segments connecting the ring structures with each other. The first and second sets of flex connector segments are oriented to permit rotation of the second ring structure about the longitudinal axis during radial expansion of the stent.

The flex connector segments may be oriented such that they are generally non-parallel to the longitudinal axis when the stent is in the collapsed state and are each generally parallel with the longitudinal axis when the stent is in the expanded state. Additionally, the connector segments may be oriented such that the first set of flex connector segments and the second set of flex connector segments are generally non-parallel with each other when the stent is in the collapsed state and are generally parallel with each other when the stent is in the expanded state.

The plurality of ring structures may further include fourth, fifth, and sixth ring structures, and the plurality of connector segments may further include third and fourth sets of flex connector segments connecting the ring structures with each other. The third and fourth sets of flex connector segments are oriented to permit rotation of the fifth ring structure about the longitudinal axis during radial expansion of the stent. In this design, during radial expansion of the stent, the first and second sets of flex connector segments may be oriented to permit rotation of the second ring structure about the longitudinal axis in a first direction and the third and fourth sets of flex connector segments may be oriented to permit rotation of the fifth ring structure about the longitudinal axis in a second direction.

In yet another aspect, the main body has a plurality of cell modules, including a diamond cell module and a flex cell module. The diamond cell module includes first and second diamond ring structures and a pair of diamond connector segments joining the first and second diamond ring structures. The diamond connector segments each cooperate with one of the first and second diamond ring structures to define a diamond-shaped portion when the stent is in the expanded state. The flex cell module includes first, second, and third flex ring structures and first and second sets of flex connector segments connecting the flex ring structures with each other. The first and second sets of flex connector segments are oriented to permit rotation of the second flex ring structure about the longitudinal axis during radial expansion of the stent.

Further objects, features and advantages of this invention will become readily apparent to persons skilled in the art after a review of the following description, with reference to the drawings and claims that are appended to and form a part of this specification.

DETAILED DESCRIPTION

The following description of preferred embodiments of the invention provides examples of the present invention. The embodiments discussed herein are merely exemplary in nature, and are not intended to limit the scope of the invention in any manner. Rather, the description of these preferred embodiments serves to enable a person of ordinary skill in the relevant art to make and use the present invention.

Figure 1:
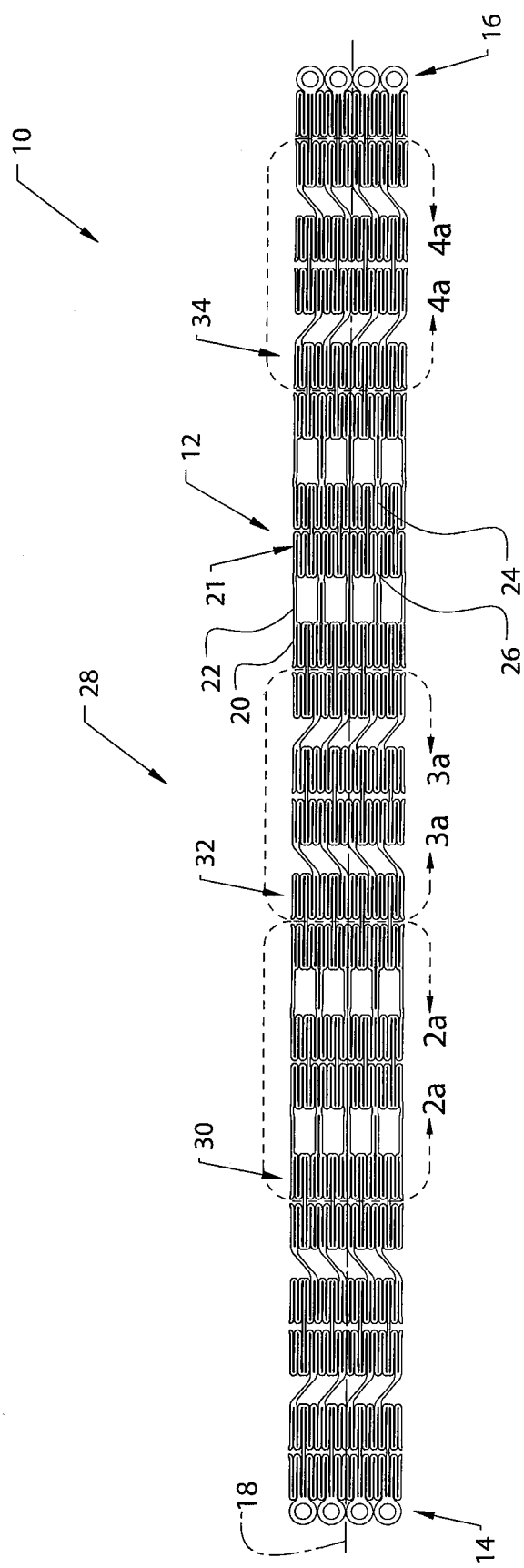
FIG. 1 is a flat pattern view of a stent embodying the principles of the present invention and shown in a collapsed state.

FIG. 1 illustrates a stent 10 according to a first preferred embodiment of the invention. The stent 10 includes a main body 12 having a first end 14, a second end 16, and a longitudinal axis 18 extending between the ends 14, 16. The main body 12 includes a plurality of ring structures 20 that are interconnected by a plurality of connector segments 22.

Each ring structure 20 is a substantially circular ring having an endless, undulating pattern. Preferably, the undulating pattern includes a serpentine pattern 21. Even more preferable, the pattern is formed by a wire having a plurality of generally linear, middle portions 24 connected to generally U-shaped or V-shaped end portions 26. As used herein, the term wire refers to any filamentary member, including, but not limited to, drawn wire and filaments laser cut from a cannula. The ring structures 20 shown in the figures are each single, unitary components.

As mentioned above, the ring structures 20 are interconnected to form the stent 10 by a plurality of connector segments 22. As illustrated in FIG. 1, each connector segment 22 joins adjacent ring structures 20. Preferably, each connector segment 22 is connected to an end portion 26 of the respective ring structures 20. Even more preferably, all of the ring structures 20 and all of the connector segments 22 are formed as a single, unitary component.

The stent 10 is an expandable stent having radially collapsed and expanded states. As such, the stent 10 can be either a self-expanding stent, such as one fabricated from a shape memory material such as Nitinol, or a balloon expandable stent. FIGS. 1, 2a, 3a, and 4a illustrate the stent 10 in its radially collapsed state. For example, in one configuration, the radial dimension of the stent 10 is minimized when the stent 10 is in the collapsed state. Alternatively, the stent 10 may have radial dimension that is greater than its minimum radial dimension when in the collapsed state. The stent 10 is typically in the collapsed state during placement into and navigation through a body vessel.

Figure 2A:
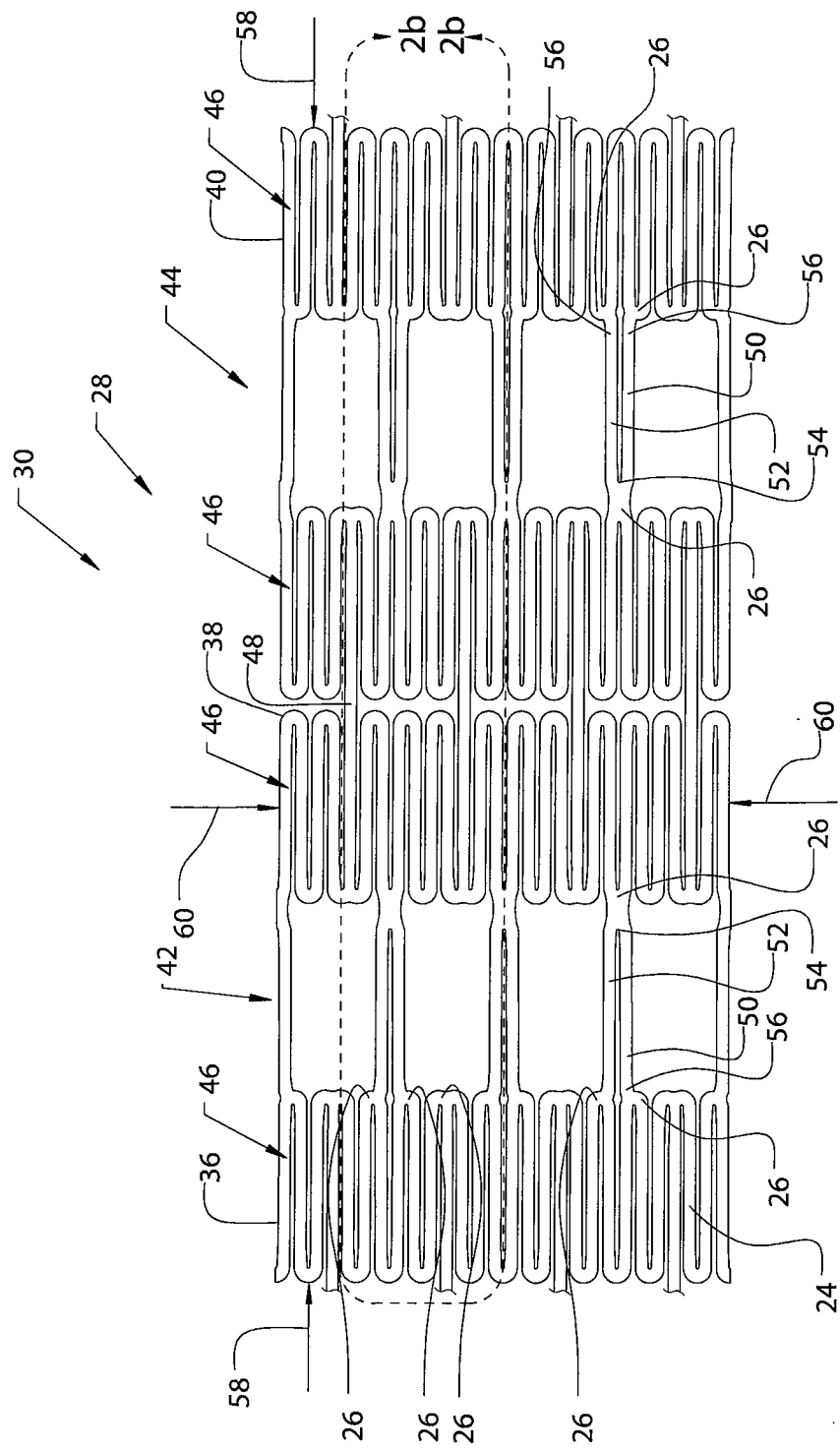
FIG. 2a is a magnified view of a diamond cell module of the stent shown in FIG. 1 in a collapsed state.
Figure 2B:
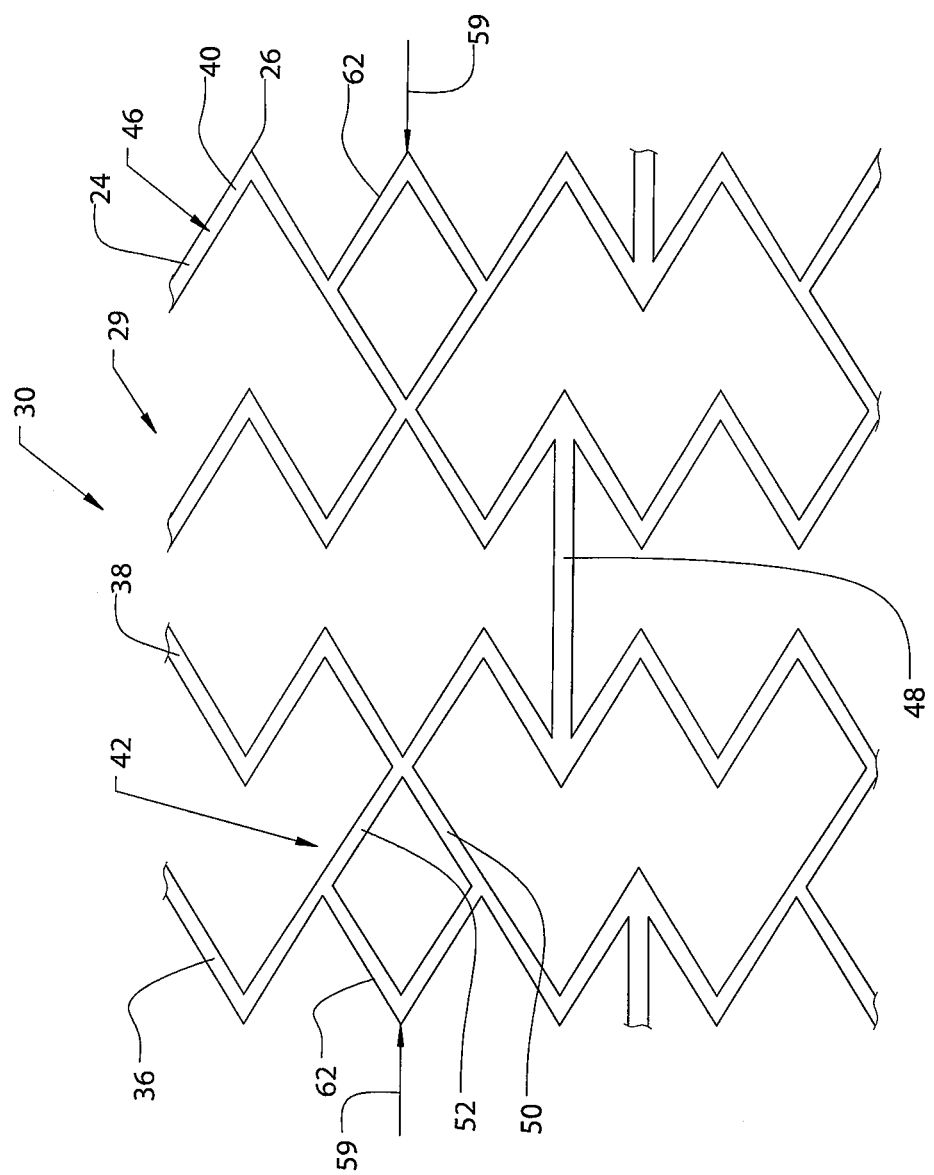
FIG. 2b is a magnified view of a portion of the diamond cell module shown in FIG. 2a in an expanded state.
Figure 3A:
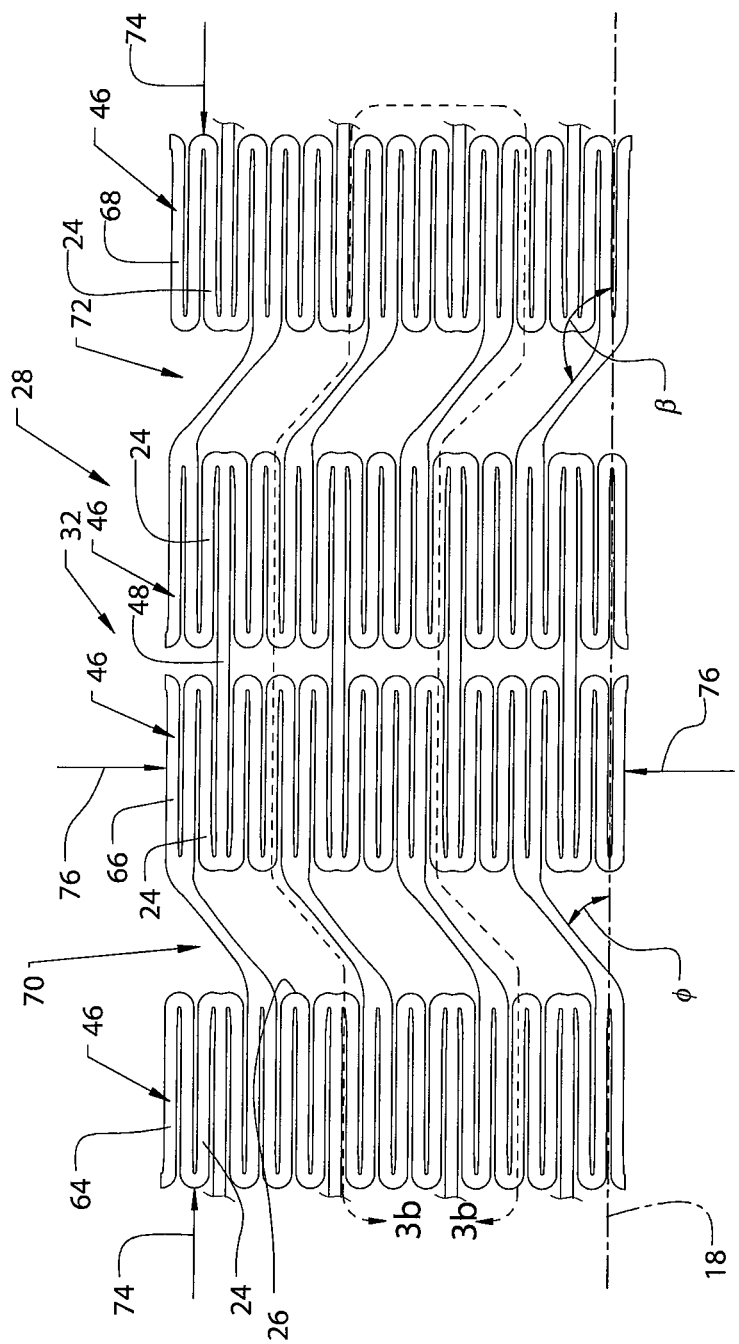
FIG. 3a is a magnified view of a flex-down cell module of the stent shown in FIG. 1 in a collapsed state.
Figure 3B:
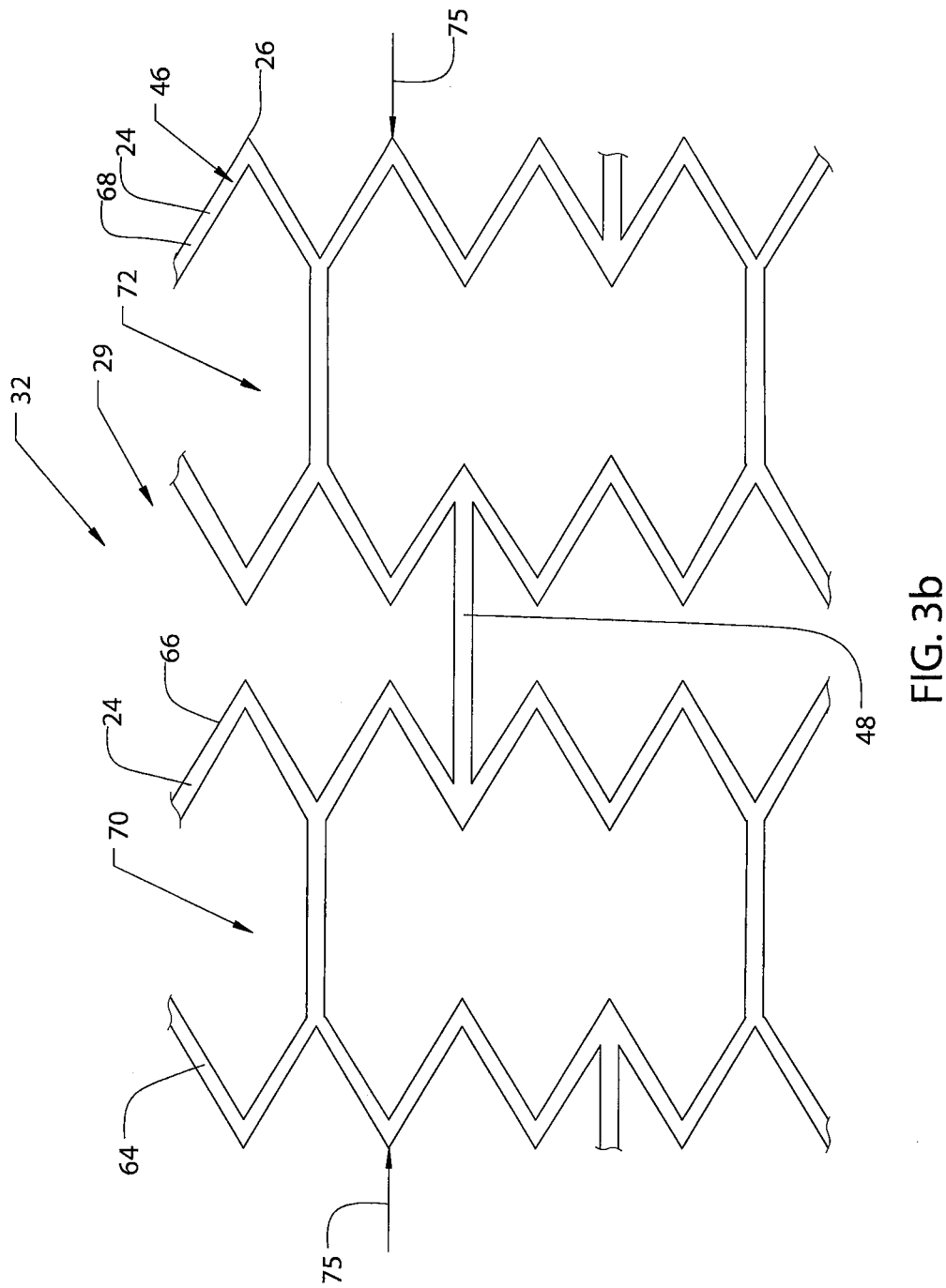
FIG. 3b is a magnified view of a portion of the flex-down cell module shown in FIG. 3a in an expanded state.
Figure 4A:
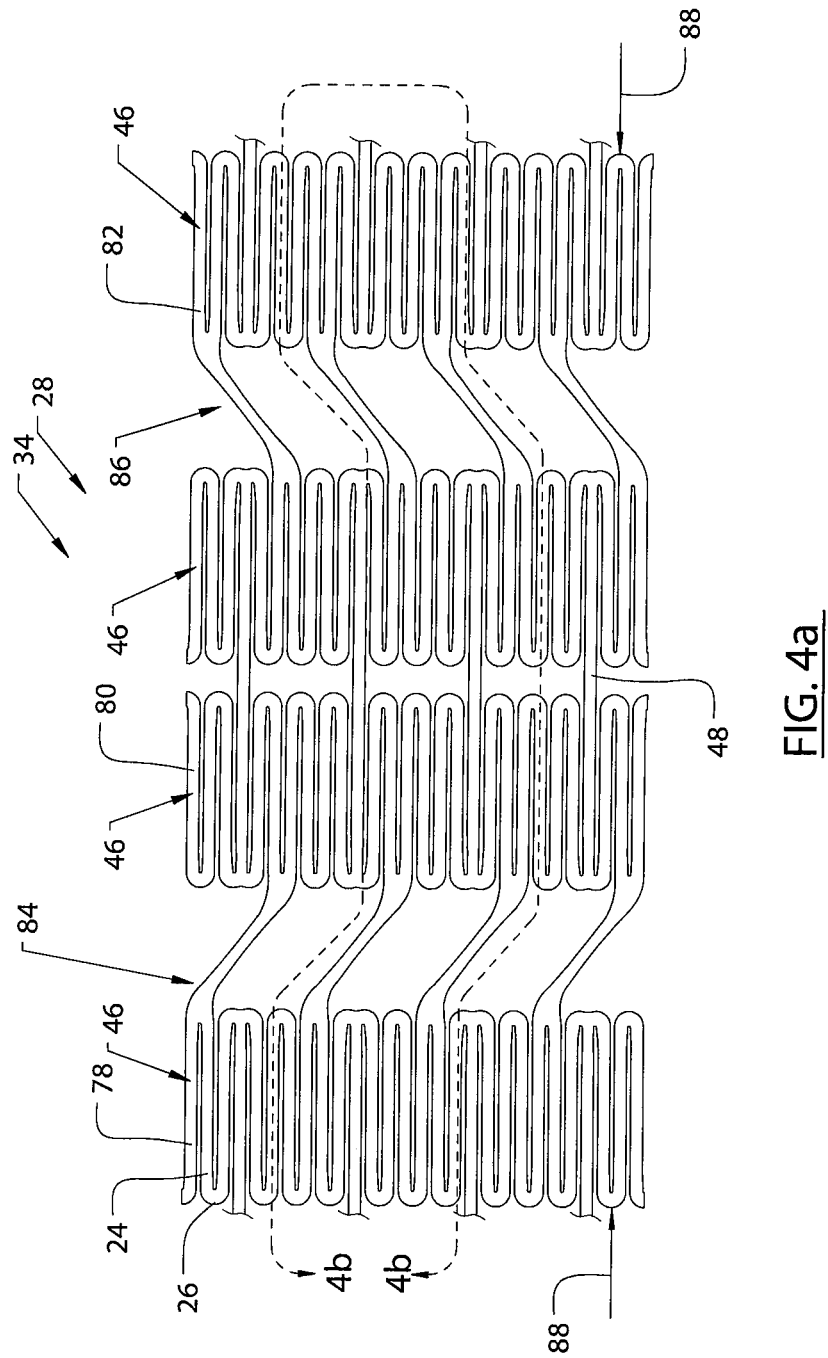
FIG. 4a is a magnified view of a flex-up cell module of the stent shown in FIG. 1 in a collapsed state.
Figure 4B:
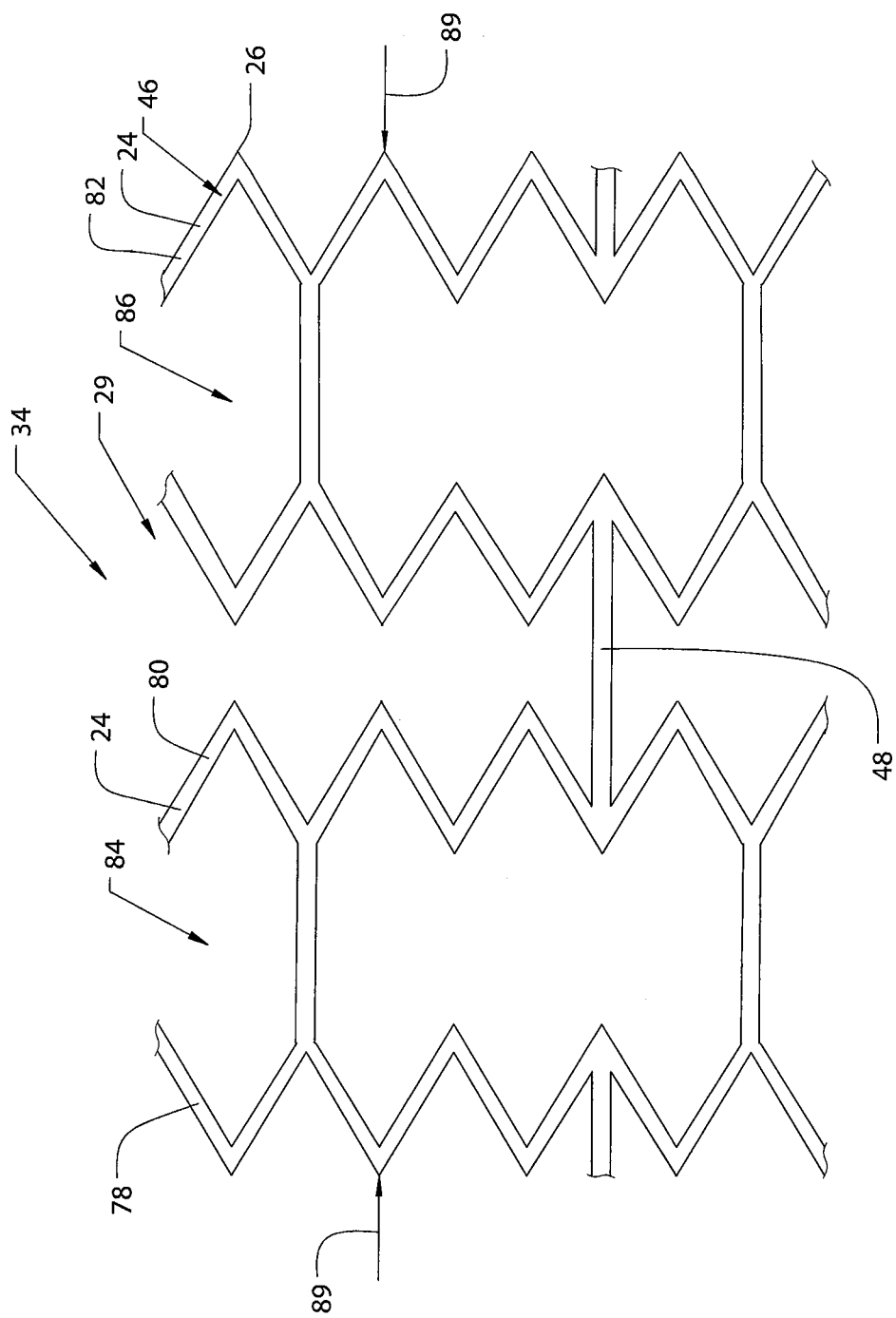
FIG. 4b is a magnified view of a portion of the flex-up cell module shown in FIG. 4a in an expanded state.

FIGS. 2b, 3b, and 4b illustrate the stent 10 in its radially expanded state. For example, in one configuration, the radial dimension of the stent 10 is maximized when the stent 10 is in the expanded state. Alternatively, the stent 10 may have radial dimension that is less than its maximum radial dimension when in the expanded state. The stent 10 is typically in the expanded state when it is positioned within the body vessel so as to providing radial support for the portion of the body vessel to be treated.

The figures show different types of ring structures 20 and different types of connector segments 22 that cooperate to define different types of cell modules. For example, FIGS. 1, 2a, and 2b show a diamond cell module 30; FIGS. 1, 3a, and 3b show a flex-down module 32; and FIGS. 1, 4a, and 4b show a flex-up module 34. The stent 10 is configured such that diamond cell modules 30 are alternated with flex-down and flex-up modules 32, 34, respectively.

FIG. 2a shows the diamond cell module 30 in the collapsed state. The diamond module 30 includes a first ring structure 36, a second ring structure 40, and a middle stent portion 38 positioned therebetween. The ring structures 36, 40 and the middle stent portion 38 are connected to each other by first and second sets of diamond connector segments 42, 44. The middle stent portion 38 includes a pair of ring structures joined by a plurality of connectors 48. The middle portions 24 of each of the ring structures 26, 38a, 38b, 40 are generally parallel with each other in the collapsed state so as to minimize the collapsed radius of the stent. More specifically, the ring structures 26, 38a, 38b, 40 shown in the figures each generally define an undulating pattern.

Although the middle stent portion 38 shown in FIG. 2a includes two ring structures 38a, 38b, the middle stent portion 38 may have any suitable number of ring structures, such as one, three, or more. Additionally, the diamond cell module 30 may include any suitable combination of ring structures and middle stent portions, such as two ring structures and no middle stent portions.

The first and second sets of diamond connector segments 42, 44 each include multiple pairs of connector segments 50, 52, where both of the pairs of connector segments 50, 52 are connected to a single ring segment end portion 26 at a first end 54 and where the respective connector segments 50, 52 are connected to separate, adjacent ring segment end portions 26 at the other end 56. This configuration causes the pairs of diamond connector segments 50, 52 to cooperate with the ring structures 36, 38, 40 to define diamond shaped portions 62 (FIG. 2b) when the stent 10 is in an expanded state, as is discussed in more detail below.

The pairs of diamond connector segments 50, 52 shown in the figures are connected to some of the ring segment end portions 26, rather than all of the ring segment end portions 26. For example, two of every three end portions 26 of the first ring structure 36 are connected to pairs of diamond connector segments 50, 52 and one out of every three end portions 26 of the middle stent portion 38 is connected to pairs of diamond connector segments 50, 52. This configuration provides an increased axial flexibility of the stent 10 compared to a design where each of the end portions 26 is connected to the pairs of diamond connector segments 50, 52. Alternatively, any suitable number of connection points may be used. The diamond module 30 defines a collapsed state length 58 measured along the longitudinal axis 18.

FIG. 2b shows a portion of the diamond cell module 30 in the expanded state. More specifically, the middle portions 24 expand to be non-parallel with each other so as to maximize the radius of the stent 10. Additionally, the pairs of diamond connector segments 50, 52 cooperate with the ring structures 36, 40 and the middle stent portion 38 to expand into the diamond shaped portions 62. The diamond portions 62 increase the radial strength of the stent 10 without requiring an increased expanded state diameter. When the radius of the diamond cell module 30 increases, the module has an expanded state length 59 that is less than the collapsed state length 58 due to foreshortening of the diamond portions 62. Therefore, the diamond cell module 30 is preferably paired with one or more flex modules shown in FIGS. 3a-4b, which each have an increasing length as the stent 10 radially expands.

FIG. 3a shows the flex-down module 32 in the collapsed state. The flex-down cell module 32 includes a first ring structure 64, a second ring structure 68, and a middle stent portion 66 positioned therebetween. The ring structures 64, 68 and the middle stent portion 66 are connected to each other by first and second sets of flex connector segments 70, 72. The middle stent portion 66 includes a pair of ring structures joined by a plurality of connectors 48. The middle portions 24 of each of the ring structures 64, 66a, 66b, 68 are generally parallel with each other so as to minimize the radius of the stent when in the collapsed state. More specifically, the ring structures 64, 66a, 66b, 68 shown in the figures each generally define an undulating pattern.

Although the middle stent portion 66 shown in FIG. 3a includes two ring structures 66a, 66b, the middle stent portion 66 may have any suitable number of ring structures, such as one, three, or more. Additionally, the flex-down cell module 32 may include any suitable combination of ring structures and middle stent portions, such as two ring structures and no middle stent portions.

The first and second sets of flex connector segments 70, 72 are each non-parallel with each other and non-parallel with the longitudinal axis 18 when the stent 10 is in the collapsed state. More specifically, each of the segments in the first set of flex connector segments 70 defines an angle Ø with respect to the longitudinal axis 18 and each of the segments in the second set of flex connector segments 72 defines an angle β with respect to the longitudinal axis 18, where Ø and β are supplementary angles. In other words, Ø+β=180°. In the figures, Ø=30° and β=150°, but any of the sets of segments 70, 72 may have any suitable angular position with respect to the longitudinal axis 18. The supplementary angle relationship between the sets of segments 70, 72 causes the respective sets of segments 70, 72 to urge the middle stent portion 66 with generally equal forces during expansion of the stent 10. More specifically, when the stent 10 expands, the respective sets of segments 70, 72 straighten with respect to the longitudinal axis and urge the middle stent portion 66 in a downward motion in the flat pattern view of FIG. 3a. The respective sets of segments 70, 72 may straighten due to shape memory or due to flex points in the flex-down module 32, such as decreased thickness of the wire at the ends of the segments 70, 72. When the stent 10 is in its actual, tubular shape, the middle stent portion 66 is urged to rotate about the longitudinal axis 18 in a clockwise direction when viewed from the left side of FIG. 3a. The flex-down module 32 defines a collapsed state length 74 measured along the longitudinal axis 18.

Figure 6:
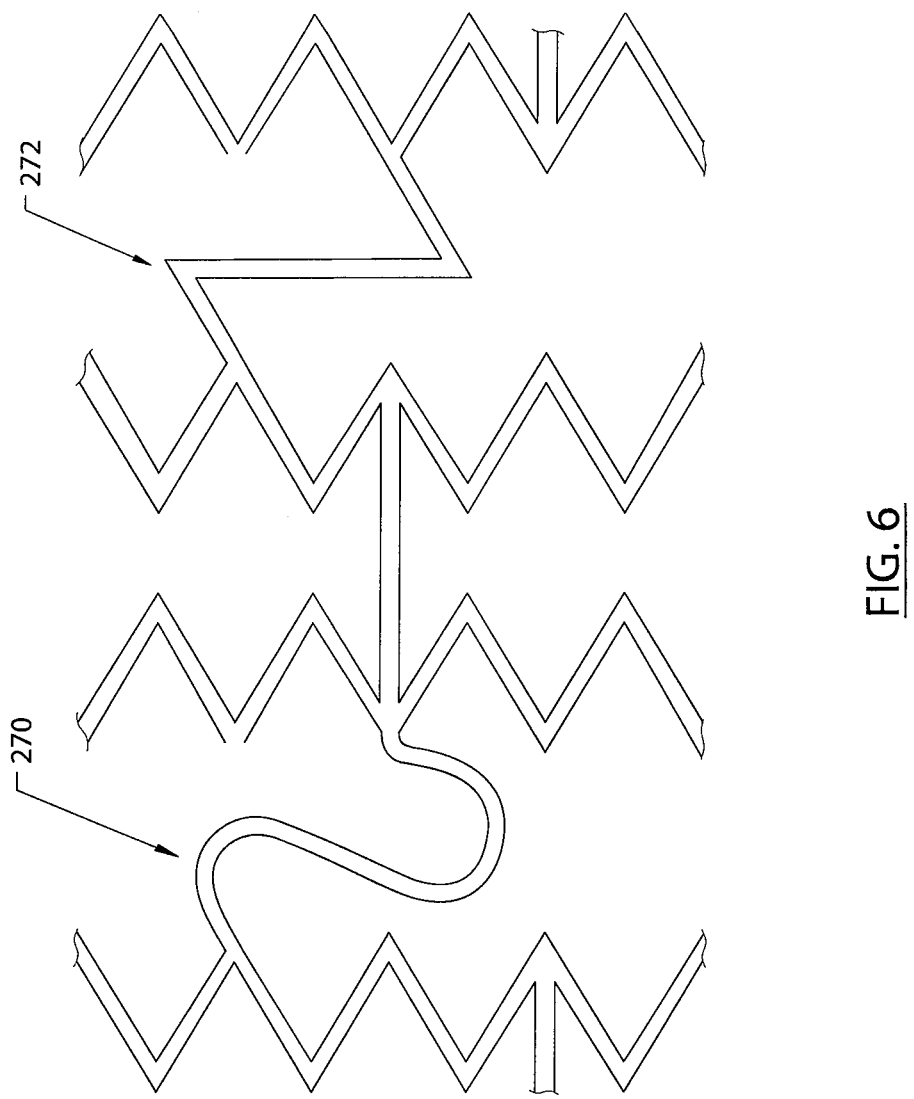
FIG. 6 is a magnified view of a portion of another stent embodying the principles of the present invention and shown in an expanded state.

The individual segments of each of the sets of segments 70, 72 are connected to some of the ring segment end portions 26, rather than all of the ring segment end portions 26. For example, one of every three end portions 26 of the ring structures 64, 68 and the middle stent portion 66 are connected to flex connector segments 70, 72. Alternatively, any suitable configuration may be used. As another alternative design, and as is shown in FIG. 6, connector segments 270, 272 may each have a non-linear shape, such as an S-shape or a Z-shape.

FIG. 3b shows a portion 32a of the flex-down module 32 in the expanded state. More specifically, the middle portions 24 expand to be non-parallel with each other so as to maximize the radius of the stent 10. Additionally, the individual segments of each of the sets of segments 70, 72 pivot to be generally parallel with the longitudinal axis 18 as the stent 10 expands. Therefore, as the radius of the flex-down module 32 increases, the module has an expanded state length 75 that is greater than the collapsed state length 74 due to effective lengthening of the sets of segments 70, 72. Therefore, the lengthening of the flex-down module 32 and the foreshortening of the diamond cell module 30 at least partially counteract each other to minimize length change of the stent 10 during radial expansion.

FIG. 4a shows the flex-up module 34 in the collapsed state. The flex-up module 34 has a similar structure and function to the flex-down module 32, except the middle stent portion 80 in the flex-up module 34 is urged in an opposite direction than the middle stent portion 66 in the flex-down module 32 during radial expansion.

The flex-up module 34 includes a first ring structure 78, a second ring structure 82, and a middle stent portion 80 positioned therebewteen. The ring structures 78, 82 and the middle stent portion 80 are connected to each other by first and second sets of flex connector segments 84, 86. The middle stent portion 80 includes a pair of ring structures 80a, 80b joined by a plurality of connectors 48. The middle portions 24 of each of the ring structures 78, 80a, 80b, 82 are generally parallel with each other so as to minimize the radius of the stent when in the collapsed state. More specifically, the ring structures 78, 80a, 80b, 82 shown in the figures each generally define an undulating pattern.

Although the middle stent portion 80 shown in FIG. 4a includes two ring structures 80a, 80b, the middle stent portion 80 may have any suitable number of ring structures, such as one, three, or more. Additionally, the flex-up cell module 34 may include any suitable combination of ring structures and middle stent portions, such as two ring structures and no middle stent portions.

The first and second sets of flex connector segments 84, 86 are each non-parallel with each other and non-parallel with the longitudinal axis 18 when the stent 10 is in the collapsed state. Additionally, each of the segments in the first set of flex connector segments 84 defines the supplementary angle of the segments in the second set of flex connector segments 86. However, the first and second sets of flex connector segments 84, 86 are oriented opposite the first and second sets of flex connector segments 70, 72 shown in FIGS. 2a and 2b so that the middle stent portion 80 shown in FIG. 4a is urged in a counterclockwise direction, as viewed from the left side of FIG. 4a, as the stent 10 radially expands. The opposite rotation of the flex-up and flex-down segments 32, 34 localizes the rotational movement and minimizes the overall rotation of the stent 10. The flex-up module 34 defines a collapsed state length 88 measured along the longitudinal axis 18.

FIG. 4b shows a portion 34a of the flex-up module 34 in the expanded state. More specifically, the middle portions 24 expand to be non-parallel with each other so as to maximize the radius of the stent 10. Additionally, the individual segments of each of the sets of segments 84, 86 pivot to be generally parallel with the longitudinal axis 18 as the stent 10 expands. Therefore, as the radius of the flex-up module 34 increases, the module has an expanded state length 89 that is greater than the collapsed state length 88 due to effective lengthening of the sets of segments 84, 86. Therefore, the lengthening of the flex-down module 32 and flex-up module 34 cooperate to counteract the foreshortening of the diamond cell module 30 to minimize length change of the stent 10 during radial expansion.

The stent 10 shown in FIG. 1 is configured to have a generally constant longitudinal length in the collapsed state and the expanded state. For example, the flex-down modules 32 and the flex-up modules 34 shown in FIG. 1 are configured to counteract the collective foreshortening of the diamond cell modules 30 during radial expansion. More specifically, the modules 30, 32, 34 have foreshortening/forelengthening ratios such that three flex modules (two flex-up modules 34 and one flex-down module 32) are able to compensate for the foreshortening of two diamond cell modules 30 such that the stent 10 length remains generally constant in the collapsed state and the expanded state. However, modules 30, 32, 34 having other ratios may be utilized with the present invention.

Figure 5A:
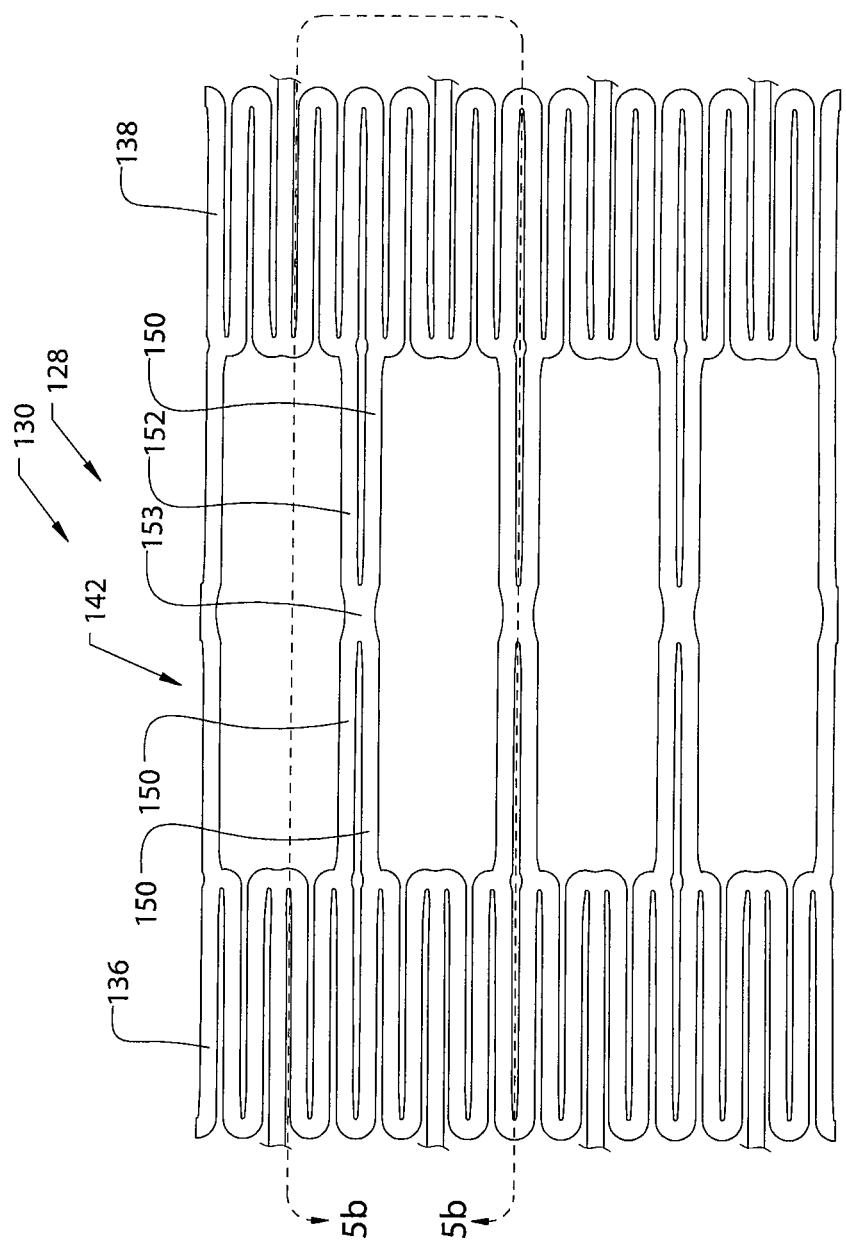
FIG. 5a is a flat pattern view of a diamond cell module of another stent embodying the principles of the present invention and shown in a collapsed state.
Figure 5B:
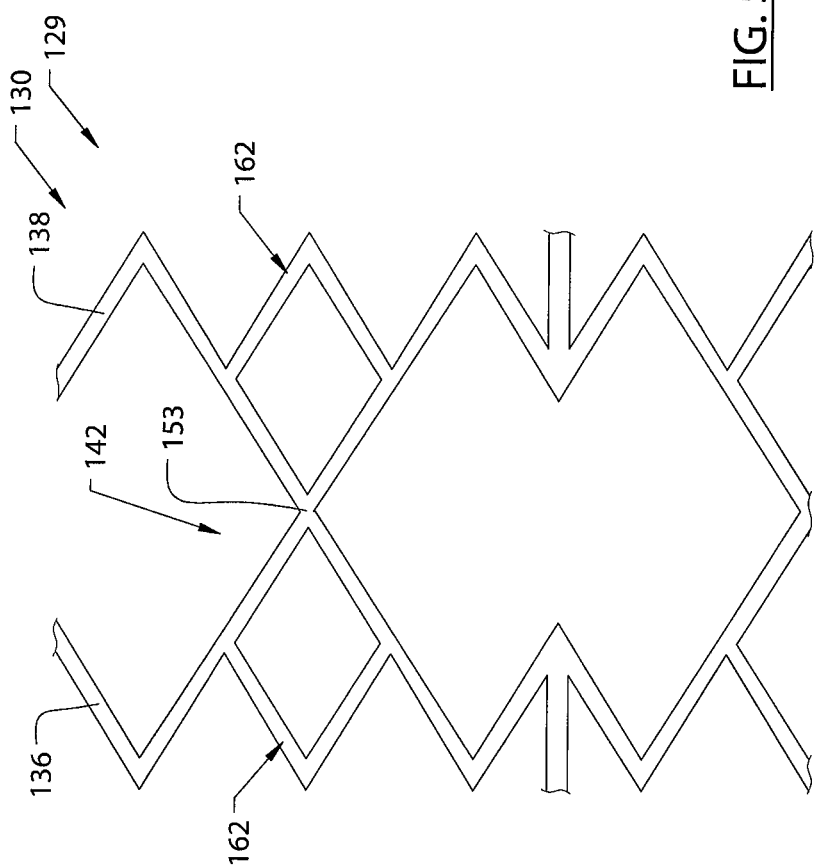
FIG. 5b is a magnified view of a portion of the diamond cell module shown in FIG. 5a in the expanded state.

FIG. 5a shows an alternative diamond cell module 130 in the collapsed state and FIG. 5b shows a portion 130a of the diamond cell module 130 in the expanded state. The diamond module 130 includes a first ring structure 136 and a second ring structure 138 joined by a set of diamond connector segments 142. The set of diamond connector segments 142 includes multiple pairs of connector segments 150, 152 with a connection point 153 between the pairs of segments 150, 152 so that the pairs of connector segments 150, 152 cooperate with the first and second ring structures 136, 138 to define two diamond shaped portions 162 when the stent is in the expanded state 129. The two diamond shaped portions 162 may provide increased radial strength over the configuration shown in FIGS. 2a and 2b.

It is therefore intended that the foregoing detailed description be regarded as illustrative rather than limiting, and that it be understood that it is the following claims, including all equivalents, that are intended to define the spirit and scope of this invention.

What is claimed is:

1. An expandable stent radially adjustable between a collapsed state and an expanded state, the stent comprising:
a main body having a first end, a second end, and a longitudinal axis extending from the first end to the second end, the main body comprising a plurality of ring structures, a middle stent portion, and a plurality of connector segments, each of the plurality of ring structures and the middle stent portion including an undulating pattern of a plurality of generally linear middle portions connected with each other by a plurality of generally U-shaped or V-shaped end portions, the middle stent portion positioned between first and second ring structures of the plurality of ring structures; and
a plurality of connector segments including at least one pair of crossed diamond connector segments joining the first ring structure and the middle stent portion by connecting two of every three end portions of the first ring structure to two of every three end portions of the middle stent portion while keeping the remaining end portion of the every three end portions of the first ring structure and of the middle stent portion free of any connector segments extending to the middle stent portion, wherein each of the at least one pair of diamond connector segments and the first ring structure and the middle stent portion define two diamond-shaped portions when the stent is in the expanded state.

2. An expandable stent radially adjustable between a collapsed state and an expanded state, the stent comprising:
a main body having a first end, a second end, and a longitudinal axis extending from the first end to the second end, the main body comprising a first stent portion and a plurality of ring structures, the plurality of ring structures including a first ring structure, and a second ring structure; and
a plurality of connector segments comprising a plurality of first flex connector segments with first end joints joining the first ring structure to an end of a first stent portion and a plurality of second flex connector segments with second end joints joining the second ring structure to another end of the first stent portion, wherein in the collapsed state a connecting line of the first end joints of each of the first flex connector segments has a first orientation and a connecting line of the second end joints of each of the second flex connector segments has a second orientation, the first and second orientations forming equal, opposite, oblique angles relative to the longitudinal axis, both orientations configured to urge rotation of the stent portion about the longitudinal axis during radial expansion of the stent and are generally non-parallel to the longitudinal axis when the stent is in the collapsed state and are generally parallel with the longitudinal axis when the stent is in the expanded state.

3. An expandable stent as in claim 1, wherein the first flex connector segments and the second flex connector segments are each generally Z-shaped or S-shaped.

4. An expandable stent as in claim 1, wherein the first flex connector segments are generally non-parallel with the second flex connector segments when the stent is in the collapsed state and are generally parallel with each other when the stent is in the expanded state.

5. An expandable stent as in claim 1, wherein the second ring structure includes a plurality of ring structures connector to each other.

6. An expandable stent as in claim 1, further comprising a second stent portion, wherein the plurality of ring structures further includes a third ring structure, and a fourth ring structure, and wherein the plurality of connector segments further includes third flex connector segments connecting the third ring structure with an end of the second stent portion and fourth flex connector segments connecting the fourth ring structure with another end of the second stent portion, wherein the third and fourth flex connector segments are oriented to urge rotation of second stent portion about the longitudinal axis during radial expansion of the stent.

7. An expandable stent as in claim 6, wherein the first and second flex connector segments are oriented to urge rotation of the first stent portion about the longitudinal axis in a first direction and the third and fourth flex connector segments are oriented to urge rotation of the second stent portion about the longitudinal axis in a second direction during radial expansion of the stent.

8. An expandable stent as in claim 6, wherein the first and second stent portions each comprise a further plurality of ring structures.

9. An expandable stent radially adjustable between a collapsed state and an expanded state, the stent comprising:
a main body having a first end, a second end, and a longitudinal axis extending from the first end to the second end, the main body comprising a plurality of cell modules generally aligned with each other along the longitudinal axis, the cell modules including:
a diamond cell module including a first diamond ring structure, a second diamond ring structure, and a pair of diamond connector segments joining the first and second diamond ring structures, each of the first and second diamond ring structures having an undulating pattern, and the diamond connector segments cooperating with the first and second diamond ring structures to define two diamond-shaped portions when the stent is in the expanded state; and
a flex cell module including a first flex ring structure, a second flex ring structure, a third flex ring structure, a first set of flex connector segments connecting the first flex ring structure with the second flex ring structure, and a second set of flex connector segments connecting the second flex ring structure with the third flex ring structure, wherein in the collapsed state the first set of flex connector segments has a first orientation and the second set of flex connector segments has a second orientation, the first and second orientations forming equal, opposite, oblique angles relative to the longitudinal axis, both orientations configured to urge rotation of the second flex ring structure about the longitudinal during radial expansion of the stent and are generally non-parallel to the longitudinal axis when the stent is in the collapsed state and are generally parallel with the longitudinal axis when the stent is in the expanded state.

10. An expandable stent as in claim 9, wherein the diamond cell module is configured to longitudinally contract a first distance and the flex cell module is configured to longitudinally lengthen a second distance during radial expansion of the stent.

11. An expandable stent as in claim 10, wherein the first distance is generally equal to the second distance so that the expandable stent maintains a generally constant length when in the collapsed state and in the expanded state.

12. An expandable stent as in claim 11, further comprising a plurality of diamond cell modules and a plurality of flex cell modules.

13. An expandable stent as in claim 12, wherein the stent defines a pattern of diamond cell modules and flex cell modules extending from the first end to the second end of the main body, the pattern including two diamond cell modules and a flex cell module.

14. An expandable stent as in claim 12, wherein the plurality of flex cell modules includes at least one flex-up cell module oriented to undergo rotation about the longitudinal axis in a first direction during radial expansion of the stent and at least one flex-down cell module oriented to undergo rotation about the longitudinal axis in a second direction during radial expansion of the stent.

* * * * *